United States Patent

Brand et al.

[11] Patent Number: 6,089,272
[45] Date of Patent: Jul. 18, 2000

[54] CHECK VALVE

[75] Inventors: Ilan Brand; Roy Baranes, both of Kfar Vradim, Israel

[73] Assignee: 3By Ltd., Tefen, Israel

[21] Appl. No.: 09/245,993

[22] Filed: Feb. 5, 1999

[30] Foreign Application Priority Data

Feb. 8, 1998 [IL] Israel ........................................ 123227

[51] Int. Cl.⁷ .................................................. F16K 15/14
[52] U.S. Cl. ............................................. 137/859; 137/852
[58] Field of Search ................................... 137/859, 852, 137/843

[56] References Cited

U.S. PATENT DOCUMENTS

| | | |
|---|---|---|
| 2,462,189 | 2/1949 | Hess . |
| 2,497,906 | 2/1950 | Peters et al. . |
| 2,758,609 | 8/1956 | Dickert et al. . |
| 2,908,283 | 10/1959 | Kiffer et al. . |
| 3,176,712 | 4/1965 | Ramsden . |
| 3,190,496 | 6/1965 | Weiland, Jr. et al. ................... 137/859 |
| 3,508,576 | 4/1970 | Gross ...................................... 137/859 |
| 3,599,657 | 8/1971 | Maldavs .................................. 137/859 |
| 3,710,942 | 1/1973 | Rosenberg . |
| 3,807,430 | 4/1974 | Keller ..................................... 137/859 |
| 3,827,456 | 8/1974 | Sheppard . |
| 4,003,398 | 1/1977 | Duveau . |
| 4,141,379 | 2/1979 | Manske . |
| 4,188,978 | 2/1980 | De Lorenzo ............................ 137/859 |
| 4,241,756 | 12/1980 | Bennett et al. ......................... 137/859 |
| 4,334,786 | 6/1982 | Delcoigne et al. ..................... 137/403 |
| 4,355,639 | 10/1982 | Salvo ...................................... 137/859 |
| 4,593,720 | 6/1986 | Bergandy . |
| 4,712,583 | 12/1987 | Pelmulder et al. . |
| 4,986,310 | 1/1991 | Bailey et al. ........................... 137/859 |
| 5,025,829 | 6/1991 | Edwards et al. . |
| 5,069,243 | 12/1991 | Foreman ................................ 137/205 |
| 5,269,771 | 12/1993 | Thomas et al. . |
| 5,273,546 | 12/1993 | Mc Laughlin et al. . |
| 5,305,795 | 4/1994 | Forberg .................................. 137/859 |
| 5,617,897 | 4/1997 | Myers .................................... 137/859 |
| 5,697,770 | 12/1997 | Schulz ................................... 137/859 |
| 5,727,594 | 3/1998 | Choksi ................................... 137/859 |

FOREIGN PATENT DOCUMENTS

WO 97/00399  1/1997  WIPO .

*Primary Examiner*—Denise L. Ferensic
*Assistant Examiner*—Joanne Y. Kim
*Attorney, Agent, or Firm*—Ladas & Parry

[57] ABSTRACT

A check valve (10) including a valve disk (12), wherein the valve disk (12) is so arranged and configured as to be of a thickness sufficiently substantial to prevent the valve disk (12) from exhibiting a significant amount of flexure even under high reverse pressure, an upper housing portion (16) having an inlet aperture (18) formed therein, a lower housing portion (20) having an outlet portion (22) formed therein, the upper housing portion (16) being formed with a valve seat (24) which protrudes towards the lower housing portion (20) by a preselected distance, the inlet aperture (18) extending through the valve seat (24), a static seal ring (26) for installation between the upper (16) and lower (20) housing portions in sealing fashion, the static seal ring (26) being located circumferentially around and spaced away from the valve disk (12), and a support web (32) extending between the static seal ring (26) and the valve disk (12) for supporting the valve disk (12) from the static seal ring (26), the support web (32) being flat when in an unbiased position, the support web (32) being elastomeric and functioning to bias and maintain the valve disk (12) against the valve seat (24) of the upper housing portion (16) around the inlet aperture (18) in sealing fashion until and unless a predetermined forward pressure drop exists across the valve (10), the support web (32) having disposed therein a plurality of apertures (36) to allow the passage of a fluid therethrough.

9 Claims, 1 Drawing Sheet

CHECK VALVE

FIELD OF THE INVENTION

The present invention relates generally to apparatus for regulation of fluid flow in medical applications and particularly to check valves and anti-free-flow valves for such apparatus.

BACKGROUND OF THE INVENTION

Infusion pumps are well known devices used to administer drugs to a patient in small, metered doses at frequent intervals or, alternatively, in the case of some devices, at a low but essentially continuous rate. Infusion pump therapy may be electronically controlled to deliver precise, metered doses at exactly determined intervals, thereby providing a beneficial gradual infusion of medication to the patient. In this manner, the infusion pump is able to mimic the natural process whereby chemical balances are maintained precisely by operating on a continuous time basis.

One of the essential elements of an infusion pump is a one-way valve, also known as a check valve or anti-free-flow valve, one or more of which may be required in virtually any design for an infusion pump. Such a valve must be highly precise, operating in a passive manner to open with a relatively small break pressure or cracking pressure in the desired direction of flow through the valve. The valve must also be resistant to a substantially higher reverse pressure, not opening or leaking at all, since any reverse flow in the opposite direction would result a reduction in the amount of medication being delivered, and an imprecise infusion pump which would be totally unacceptable.

U.S. Pat. No. 2,462,189 to Hess, U.S. Pat. No. 2,497,906 to Peters et al., U.S. Pat. No. 4,141,379 to Manske, and U.S. Pat. No. 4,593,720 to Bergandy describe check valves.

One of the better known check valves of the art is described in U.S. Pat. No. 4,712,583 to Pelmulder et al., the disclosure of which is incorporated herein by reference. The valve of Pelmulder et al. is molded in a unitary fashion of a medical grade elastomer such as silicone rubber. A circular valve disk has on the top side thereof a protruding cylindrical dynamic sealing ridge, which is the actual valve element. A static seal ring having a larger inner diameter than the outer diameter of the valve disc is located concentrically around the valve disk. The valve disk is supported from the static seal ring by a thin support web extending between the static support ring and the valve disk, which web has a plurality of holes therethrough to allow fluid passage.

The valve is installed by locating it in a first housing portion which has provision, such as an annular groove, for receiving the static seal ring, and which also includes a web support structure for supporting a portion of the web adjacent to the static seal ring. The first housing portion has an aperture therein to allow fluid passing through the valve to exit, which aperture is located on the underside of the valve when it is installed in the first housing portion as described above.

A lower housing portion is then installed on top of the valve as previously installed in the first housing portion. The second housing portion, which rests on top of the valve, is essentially flat, and has an aperture therein through which fluid may enter towards the valve. This aperture is located above the valve disk and concentrically within the dynamic sealing ridge. When the lower housing portion is installed onto the first housing portion with the valve therebetween, the static seal ring is compressed to create a good seal.

In operation, when the pressure is greater on top of the valve disk than under the valve disk, the valve will tend to open, requiring only a small pressure to operate. However, when this small break pressure is not present, or when a reverse pressure is present, the valve will remain in a closed position. The valve thus has a positive sealing action when closed, and opens easily when the small crack pressure (or a greater pressure in that direction) is present.

It is essential in the teachings of Pelmulder et al. that the portion of the housing mounted on the top side of the valve be flat and that the dynamic sealing ridge be bulgy so as to space the web from the flat surface of the top housing.

U.S. Pat. No. 5,025,829 to Edwards et al., the disclosure of which is incorporated herein by reference, describes a check valve disk which comprises a flat, circular piece of flexible material. The valve disk is formed by an outer sealing ring at its periphery, at least three arcuately-shaped windows substantially evenly-spaced radially inwards from the outer sealing ring, and a circular closing member concentrically disposed radially inwards from the windows and joined to the outer sealing ring by a plurality of webs. The valve disk is installed between a first housing portion having an inlet and a valve seat, and a lower housing portion having an outlet. Both housing portions have a valve disk retaining surface with an annular ridge protruding therefrom. In such a manner, the valve disk is retained between the housing portions by the annular ridges contacting its outer sealing ring.

The valve seat which is formed in the first housing portion protrudes towards the lower housing portion by a preselected distance beneath the valve disk retaining surface in the first housing portion. In such a manner, various amounts of preloading are capable with valve disks of the same manufacture. Edwards et al. teaches constructing the valve disk as a flat, circular piece of flexible material. The housing portions are snap-fit together.

The present inventors have found that both the Pelmulder et al. check valve and the Edwards et al. check valve suffer from drawbacks. Because the Edwards et al. check valve employs a flat valve disk, it has been difficult to control accuracy of the cracking pressure. The dynamic sealing ridge of the Pelmulder et al. check valve does not satisfactorily provide accurate control of the cracking pressure either, possibly due to its elastomeric properties.

SUMMARY OF THE INVENTION

The present invention seeks to provide an improved check valve which overcomes the above drawbacks. As mentioned hereinabove, the Pelmulder et al. check valve uses the dynamic sealing ridge to flex the valve disk away from the upper housing portion. Unlike the prior art, the present invention uses a rigid valve seal formed in the upper housing portion to space the valve disk away from the upper housing portion. Although a similar valve seat is present in Edwards et al., nevertheless the novel structure of the present invention provides an unexpected and significant improvement in performance over the structures of Pelmulder et al. and Edwards et al. The present inventors have found that the present invention provides a significant increase over the prior art in controlling accuracy of cracking pressure.

There is thus provided in accordance with a preferred embodiment of the present invention a check valve including a valve disk, wherein the valve disk is so arranged and configured as to be of a thickness sufficiently substantial to prevent the valve disk from exhibiting a significant amount of flexure even under high reverse pressure, an upper housing portion having an inlet aperture formed therein, a lower housing portion having an outlet portion formed therein, the upper housing portion being formed with a valve seat which protrudes towards the lower housing portion by a preselected distance, the inlet aperture extending through the valve seat, a static seal ring for installation between the upper and lower housing portions in sealing fashion, the static seal ring being located circumferentially around and spaced away from the valve disk, and a relatively thin support web extending between the static seal ring and the valve disk for supporting the valve disk from the static seal ring, the support web being flat when in an unbiased position, the support web being elastomeric and functioning to bias and maintain the valve disk against the valve seat of the upper housing portion around the inlet aperture in sealing fashion until and unless a predetermined forward pressure drop exists across the valve, the support web having disposed therein a plurality of apertures to allow the passage of fluid therethrough.

In accordance with a preferred embodiment of the present invention the lower housing portion snap-fits together with the upper housing portion. Preferably the lower housing portion includes an annular ridge which snap-fits together with an annular groove formed in the upper housing portion.

Additionally in accordance with a preferred embodiment of the present invention at least one of the lower and the upper housing portions includes a Luer-lock fitting.

Further in accordance with a preferred embodiment of the present invention the valve disk includes an elastomeric material of medical grade. The elastomeric material may be selected from the group consisting of a thermoplastic elastomer, silicone rubber, a terpolymer of ethylene, polyethylene, propylene, polyurethane and a diene side chain.

In accordance with a preferred embodiment of the present invention the elastomeric material has a durometer hardness of between 30 and 100 on the Shore A scale. Most preferably the elastomeric material has a durometer hardness of between 60 and 80 on the Shore A scale.

Further in accordance with a preferred embodiment of the present invention the valve is biased in a closed position until the forward pressure drop across the valve is at least 0.25 bar.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

Figure 1:
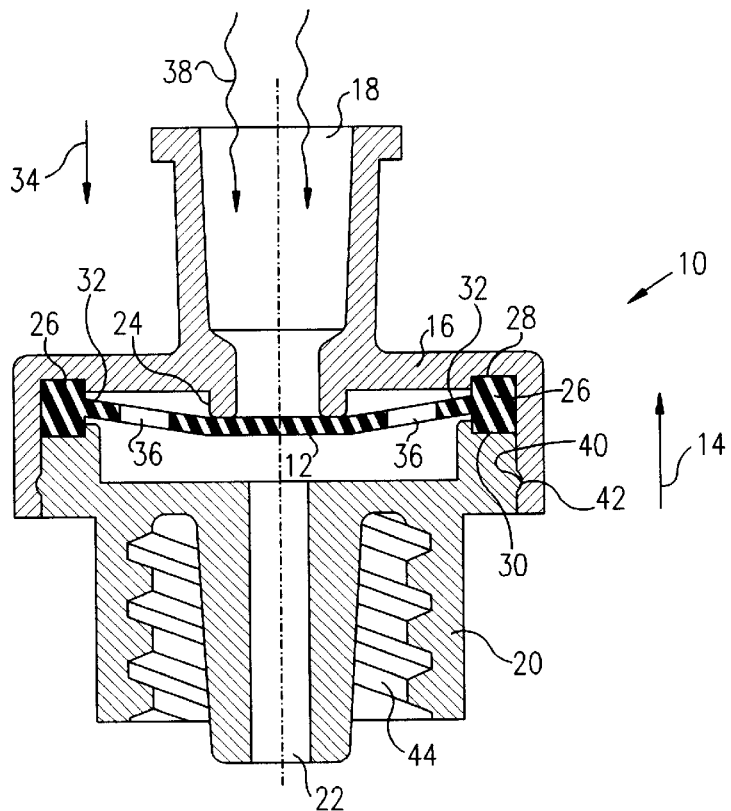
FIG. 1 is a simplified sectional illustration of a check valve constructed and operative in accordance with a preferred embodiment of the present invention, in a closed position.
Figure 2:
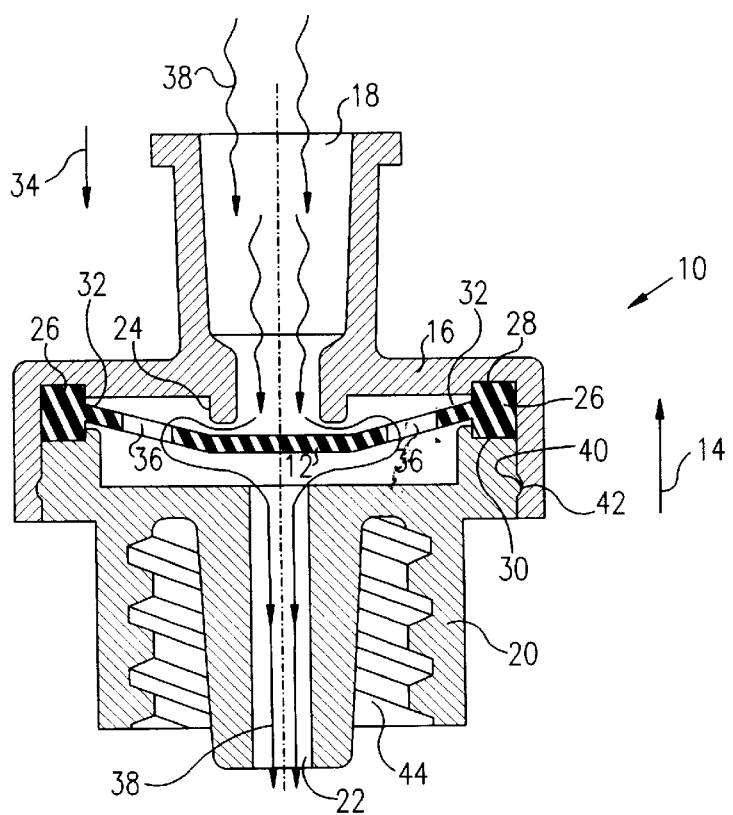
FIG. 2 is a simplified sectional illustration of the check valve of the present invention in an open position.

Reference is now made to FIGS. 1 and 2 which illustrate a check valve 10 constructed and operative in accordance with a preferred embodiment of the present invention.

Check valve 10 preferably includes a valve disk 12 formed of a flexible material and having a generally flat, circular shape. Such shape may be formed by stamping and cutting disk 12 in any conventional way or by molding disk 12. The flexible material used for valve disk 12 comprises an elastomeric material, a thermoplastic material or a thermoplastic elastomer, preferably of a medical grade. Preferably, such flexible material comprises a material having a Shore A durometer hardness in the range of about 30–100. Most preferably the elastomeric material has a durometer hardness of between 60 and 80 on the Shore A scale. Exemplary materials which may be used for valve disk 12 are selected from the group consisting of silicone rubber, terpolymers of ethylene, polyethylene, propylene, polyurethane and a diene side chain, which products have been sold under the trademarks EPT, EPSYN, ROYALENE, VISTALON and NORDEL or thermoplastic elastomers sold under the trademarks HYTRON, KRATON and SANTOPRENE. Valve disk 12 is arranged and configured as to be of a thickness sufficiently substantial to prevent exhibiting a significant amount of flexure even under high reverse pressure (in the direction of an arrow 14 in FIG. 1).

An upper housing portion 16 is provided which has an inlet aperture 18 formed therein. A lower housing portion 20 is provided which has an outlet portion 22 formed therein. Upper housing portion 16 is formed with a valve seat 24 which protrudes towards lower housing portion 20 by a preselected distance. Inlet aperture 18 extends through valve seat 24. Upper and lower housing portions 16 and 20 may be constructed of a suitable plastic such as ABS, for example.

A static seal ring 26 is provided for installation between upper and lower housing portions 16 and 20 in sealing fashion. Seal ring 26 is located circumferentially around and spaced away from valve disk 12. Preferably seal ring 26 is installed in corresponding grooves 28 and 30 formed in upper and lower housing portions 16 and 20, respectively.

A relatively thin support web 32 extends between seal ring 26 and valve disk 12 for supporting valve disk 12 from seal ring 26. Support web 32 is elastomeric and biases and maintains valve disk 12 against valve seat 24 around inlet aperture 18 in sealing fashion until and unless a predetermined forward pressure drop (in the direction of an arrow 34) exists across valve 10. Support web 32 is flat when in an unbiased position, but as seen in FIG. 1, is flexed towards lower housing portion 20 by virtue of being biased against valve seat 24, thereby providing a preload in the operation of valve 10. Support web 32 has formed therein a plurality of apertures 36 to allow passage of fluid 38 therethrough, as will be seen in FIG. 2.

Lower housing portion 20 preferably includes an annular ridge 40 which snap-fits together with an annular groove 42 formed in upper housing portion 16. Either or both of lower and upper housing portions 16 and 20 may include a Luer-lock fitting, such as designated by reference numeral 44.

Valve 10 is biased in the closed position of FIG. 1 until the forward pressure drop across the valve is at least 0.25 bar, upon which valve 10 opens to the position shown in FIG. 2.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A check valve comprising:
   a valve disk, wherein said valve disk is so arranged and configured as to be of a thickness sufficiently substantial to prevent said valve disk from exhibiting a significant amount of flexure even under high reverse pressure;

an upper housing portion having an inlet aperture formed therein;

a lower housing portion having an outlet portion formed therein, said upper housing portion being formed with a valve seat which protrudes towards the lower housing portion by a preselected distance, said inlet aperture extending through said valve seat, said valve seat being formed with a generally blunt face;

a static seal ring for installation between said upper and lower housing portions in sealing fashion, said static seal ring being located circumferentially around and spaced away from said valve disk; and a support web extending between said static seal ring and said valve disk for supporting said valve disk from said static seal ring, said support web being flat when in an unbiased position, said support web being elastomeric and functioning to bias and maintain said valve disk against the blunt face of said valve seat of said upper housing portion around said inlet aperture in sealing fashion until and unless a predetermined forward pressure drop exists across said valve, said support web having disposed therein a plurality of apertures to allow the passage of a fluid therethrough.

2. A valve according to claim 1 wherein said lower housing portion snap-fits together with said upper housing portion.

3. A valve according to claim 1 wherein said lower housing portion comprises an annular ridge which snap-fits together with an annular groove formed in said upper housing portion.

4. A valve according to claim 1 wherein at least one of said lower and said upper housing portions comprises a Luer-lock fitting.

5. A valve according to claim 1 wherein said valve disk comprises an elastomeric material of medical grade.

6. A valve according to claim 5 wherein said elastomeric material is selected from the group consisting of a thermoplastic elastomer, silicone rubber, a terpolymer of ethylene, polyethylene, propylene, polyurethane and a diene side chain.

7. A valve according to claim 5 wherein said elastomeric material has a durometer hardness of between 30 and 100 on the Shore A scale.

8. A valve according to claim 5 wherein said elastomeric material has a durometer hardness of between 60 and 80 on the Shore A scale.

9. A valve according to claim 1 wherein said valve is biased in a closed position until the forward pressure drop across said valve is at least 0.25 bar.

* * * * *